United States Patent
Prakash et al.

(12) 
(10) Patent No.: US 6,251,866 B1
(45) Date of Patent: Jun. 26, 2001

(54) CONJUGATES TARGETED TO THE INTERLEUKIN-2 RECEPTOR

(75) Inventors: Ramesh K. Prakash; Christopher M. Clemens, both of Salt Lake City, UT (US)

(73) Assignee: Watson Laboratories, Inc., Salt Lake City, UT (US)

(*) Notice: Subject to any disclaimer, the term of this patent is extended or adjusted under 35 U.S.C. 154(b) by 0 days.

(21) Appl. No.: 09/128,572

(22) Filed: Aug. 4, 1998

Related U.S. Application Data

(63) Continuation-in-part of application No. 08/914,042, filed on Aug. 5, 1997, now abandoned.

(51) Int. Cl.$^7$ .......................... A61K 38/08; A61K 47/42

(52) U.S. Cl. ............................... 514/17; 514/2; 530/300; 530/329; 530/815; 530/812; 424/278.1; 424/85.1; 930/141

(58) Field of Search ............. 514/2, 17; 530/300, 530/329, 812, 815; 424/278.1, 85.1; 930/141

(56) References Cited

U.S. PATENT DOCUMENTS

| | | | |
|---|---|---|---|
| 4,350,626 | 9/1982 | Masuho et al. | 260/112.5 R |
| 4,450,154 | 5/1984 | Masuho et al. | 530/350 |
| 4,675,382 | 6/1987 | Murphy | 260/112 R |
| 4,792,447 | 12/1988 | Uhr et al. | 424/85.91 |
| 4,906,469 | 3/1990 | Jansen et al. | 424/85.91 |
| 4,917,888 * | 4/1990 | Katre et al. | 424/85.91 |
| 4,962,188 | 10/1990 | Frankel | 530/389 |
| 5,059,413 * | 10/1991 | Reardan et al. | 424/4.1 |
| 5,135,736 | 8/1992 | Anderson et al. | 424/1.1 |
| 5,149,528 * | 9/1992 | Maraganore | 424/85.91 |
| 5,165,923 | 11/1992 | Thorpe et al. | 424/85.91 |
| 5,169,933 | 12/1992 | Anderson et al. | 530/391.3 |
| 5,258,453 * | 11/1993 | Kopecek et al. | 525/54.1 |
| 5,326,559 * | 7/1994 | Miller | 424/85.2 |
| 5,541,297 * | 7/1996 | Hansen et al. | 530/391 |
| 5,571,507 * | 11/1996 | Rubin-Kelley | 424/85 |
| 5,605,976 | 2/1997 | Martinez et al. | 525/408 |
| 5,612,460 | 3/1997 | Zalipsky | 530/391.9 |
| 5,614,549 | 3/1997 | Greenwald et al. | 514/449 |
| 5,620,884 | 4/1997 | Shorr et al. | 435/188 |
| 5,621,039 | 4/1997 | Hallahan et al. | 525/54.1 |
| 5,622,986 | 4/1997 | Greenwald et al. | 514/449 |
| 5,635,597 * | 6/1997 | Barrett et al. | 530/327 |
| 5,660,827 | 8/1997 | Thorpe et al. | . |
| 5,738,864 * | 4/1998 | Schacht | 424/426 |

FOREIGN PATENT DOCUMENTS

| | | |
|---|---|---|
| 65758/86 | 4/1987 | (AU) . |
| 283 008 B6 | 2/1995 | (CZ) . |
| 0091539A1 B1 B2 | 3/1983 | (EP) . |
| 0 187 547 A2 B1 | 7/1986 | (EP) . |
| 0 226 062 A1 | 6/1987 | (EP) . |
| WO 92/00748 A1 | 1/1992 | (WO) . |
| WO 93/24476 A1 | 12/1993 | (WO) . |
| WO 96/08263 | 3/1996 | (WO) . |
| WO 97/33618 | 9/1997 | (WO) . |
| WO 98/23306 A1 | 6/1998 | (WO) . |
| WO 98/51336 | 11/1998 | (WO) . |
| WO 99/07324 A3 | 2/1999 | (WO) . |
| WO 00/07543 | 2/2000 | (WO) . |

OTHER PUBLICATIONS

Pastan et al. Science, 254, 1173–1177, Nov. 1991.*
Lorberboum–Galski et al. Proc. Natl. Acad. Sci., USA, 85, 1922–1926, Mar. 1988.*
Duncan, R. et al. (1998). "Preclinical toxicology of a novel polymeric antitumor agent: HPMA copolymer–doxorubicin (PK1)" *Human and Experimental Toxicology* 17(2):93–104.
Mayes, A. et al. (1998). "Tailoring polymer surfaces for controlled cell behavior" *Mater. Res. Soc. Symph. Proc.* 530: 73–84.
Minko, T. et al. (1998). "Peculiarities of apoptosis induction and cell metabolism in human ovarian carcinoma cell lines exposed to free and HPMA copolymer bound adriamycin" *25th Proc. Int. Symp. Controlled Release Bioact. Mater.*, pp. 99–100.
Pimm, M. et al. (1993). "Targeting of N–(2–hydroxypropyl)methacrylamide copolymer–doxorubicin conjugate to the hepatocyte galactose–receptor in mice: Visualisation and quantification by gamma scintigraphy as a basis for clinical targeting studies" *J. Drug Targeting* 1(2):125–131.

(List continued on next page.)

*Primary Examiner*—Michael Borin
(74) *Attorney, Agent, or Firm*—Morrison & Foerster LLP

(57) ABSTRACT

A composition for intracellular delivery of a chemical agent into an interleukin-2-receptor-bearing cell, e.g. an activated T cell, includes a chemical agent and at least one copy of an interleukin-2-receptor-binding and endocytosis-inducing ligand coupled to a water soluble polymer. The ligand binds to a receptor on the interleukin-2-receptor-bearing cell and elicits endocytosis of the composition. The composition also preferably includes a spacer for coupling the chemical agent and the ligand to the polymer. Chemical agents can include cytotoxins, transforming nucleic acids, gene regulators, labels, antigens, drugs, and the like. A preferred water soluble polymer is a polyalkylene oxide, such as polyethylene glycol and polyethylene oxide, and activated derivatives thereof. The composition can further comprise a carrier such as another water soluble polymer, liposome, or particulate. Methods of using these compositions for delivering a chemical agent in vivo or in vitro are also disclosed. A method of detecting a disease, such as T-cell lymphocytic leukemia, T-cell acute lymphoblastic leukemia, peripheral T-cell lymphoma, Hodgkin's disease, or non-Hodgkin's lymphoma, associated with elevated levels of soluble IL-2 receptor is also disclosed.

27 Claims, 2 Drawing Sheets

Cozadd et al. (Monday Jan. 10, 10:30 am Eastern Time) "ALZA Corporation Announces Senior Management Promotions," at http://biz.yahoo.com/prnews/00110/ca_13 alza_pr_1.html (visited on Jan. 21, 2000).

Duncan, et al. (1988) Anticancer agents coupled to N-(2-Hydroxypropyl)methacrylamide copolymers. II. Evaluation of daunomycin conjugates in vivo against L 1210 leukaemia, *Br. J. Cancer* 57:147–156.

Omelyanenko, et al. (1990) "HPMA Copolymer–Anticancer Drug–OV–TL16 Antibody Conjugates. 1. Influence of the Method of Synthesis on the Binding Affinity to OVCAR–3 Ovarian Carcinoma Cells in Vitro," *Journal of Drug Targeting* 3:357–373.

Omelyanenko, et al. (1998) "HPMA Copolymer–Anticancer Drug–OV–TL16 Antibody Conjugates. II. Processing in Epithelial Ovarian Carcinoma Cells In Vitro," *Int. J. Cancer* 75:600–608.

Omelyanenko, et al. (1998) "Targetable HPMA Copolymer–Adriamycin Conjugates, Recognition, Internalization, and Sucellular Fate," *Journal of Controlled Release* 53:25–37.

Omelyanenko, et al. (1999) "Biorecognition of HPMA Copolymer–Adriamycin Conjugates by Lumphocytes Mediated by Synthetic Receptor Binding Epitopes," *Pharmaceutical Research* 16(7):1010–1019.

Peterson, et al. (1996) "Combination Chemotherapy and Photodynamic Therapy with N-(2-Hydroxypropyl)methacrylamide Copolymer–bound Anticancer Drugs Inhibit Human Ovarian Carcinoma Heterotransplanted in Nude Mice," *Cancer Research* (56): 3980–3985.

Rihova, B. and Kopecek, J. (1985) "Biological Properties of Targetable Poly[N-(2-Hydroxypropyl)methacrylamide]–Antibody Conjugates," *Journal of Controlled Release* 2:289–310.

Rihova, et al. (1986) "Bioaffinity Therapy with Antibodies and Drugs Bound to soluble Synthetic Polymers," *Journal of Chromotography* 376:221–233.

Rihova, et al. (1989) "Biocompatibility of N-(2-Hydroxypropyl)methacrylamide copolymers contianing adriamycin," *Biomaterials* 10:335–342.

Rihova, et al. (1990) "Selectivity of Antibody–Targeted Anthracycline Antibiotics on T Lymphocytes," *Journal of Bioactive and Compatible Polymers* 5:249–266.

Rihova, et al. (1998) "Antibody–directed Affinity Therapy Applied to the Immune System: In Vivo Effectiveness and Limited Toxicity of Daunomycin Conjugated to HPMA Copolymers and Targeting Antibody," *Clinical Immunology and Immunopathology* 46:100–114.

Subr, et al. (1986) "Degradation of Oligopeptide Sequences Connecting Poly [N-(2-Hydroxypropyl)methacrylamide] Chains by Lysosomal Cysteine Proteinases," *Journal of Bioactive and Compatible Polymers* 1:131–146.

vanderSpek, et al. "Epitope Tagging of $DAB_{389}$ New Insights into C–Domain Delivery to the Cytosol of Target Cells".

Vasey, et al. (1999). "Phase I Clinical and Pharmacokinetic Study of PK1 [N-(2-Hydroxypropyl)methacrylamide Copolymer Doxorubicin]: First Member of a New Class of Chemotherapeutic Agents–Drug–Polymer Conjugates," *Clinical Cancer Research* 5:83–94.

Pastan et al., "Recombinant Toxins for Cancer Treatment", 254 Science p. 1173 (1991).

Weigent et al., "The HTLV–III Envelope Protein Contains a Hexapeptide Homologous to a Region of Interleukin–2 That Binds to the Interleukin–2 Receptor", 139 Biochem. Biophys. Res. Commun. P. 367–374 (1986).

Reiher, III, et al., "Sequence Homology Between Acquired Immunodeficiency Syndrome Virus Envelope Protein and Interleukin 2", 83 Proc. Natl. Acad. Sci. USA pp. 9188–9192 (1986).

Taniguchi, et al., "Structure and expression of cloned cDNA for human interleukin–2", 302 Nature pp. 305–310 (1983).

Leonard, et al., "Molecular cloning and expression of cDNAs for the human interleukin–2 receptor", 311 Nature pp. 626–631 (1984).

Nikaido, et al., "Molecular cloning of cDNA encoding human interleukin–2 receptor", 311 Nature pp. 631–635 (1984).

Cosman, et al., "Cloning, sequence and expression of human interleukin–2 receptor", 312 Nature pp. 768–771 (1984).

Frankel, et al, "IL2 Fused to Lectin–Deficient Ricin is Toxic to Human Leukemia Cells Expressing the IL2 Receptor", 11 Leukemia pp. 22–30 (1997).

VanderSpek, et al., "Structure/Function analysis of the Transmembrane Domain of $DAB_{389}$ _Interleukin–2, an Interleukin–2 Receptor–targeted Fusion Toxin", 268 Journal of Biological Chemistry pp. 12077–12082 (1993).

Francis, et al., "Polyethylene Glycol Modification: Relevance of Improved Methodology to Tumour Targeting", 3 Journal of Drug Targeting pp. 321–340 (1996).

Subr, et al., "Polymers containing enzymatically degradable bonds, XII. Effect of spacer structure on the rate of release of daunomycin and adriamycin from poly [N-(2-hydroxypropyl)-methacrylamide] copolymer drug carriers in vitro and antitumour activity measured in vivo", 18 Journal of Controlled Release pp. 123–132 (1992).

Maeda, et al., "Conjugates of Anticancer Agents and Polymers: Advantages of Macromolecular Therapeutics in Vivo", vol. 3 No. 5 Bioconjugate Chemistry pp. 351–362.

Duncan, "Biological Effects of Soluble Synthetic Polymers as Drug Carriers", vol. 1 No. 4 CRC Critical Reviews in Therapeutic Drug Carrier Systems pp. 281–310.

* cited by examiner

CONJUGATES TARGETED TO THE INTERLEUKIN-2 RECEPTOR

CROSS-REFERENCE TO RELATED APPLICATIONS

This application is a continuation-in-part of application Ser. No. 08/914,042, filed Aug. 5, 1997, now abandoned.

BACKGROUND OF THE INVENTION

This invention relates to delivery of chemical agents to cells. More particularly, this invention relates to compositions and methods for intracellular delivery of chemical agents to a specific cell type, i.e. cells bearing the interleukin-2 (IL-2) receptor.

Toxins that target cell surface receptors or antigens on tumor cells have attracted considerable attention for treatment of cancer. E.g., I. Pastan & D. FitzGerald, Recombinant Toxins for Cancer Treatment, 254 Science 1173 (1991); Anderson et al., U.S. Pat. Nos. 5,169,933 and 5,135,736; Thorpe et al., U.S. Pat. No. 5,165,923; Jansen et al., U.S. Pat. No. 4,906,469; Frankel, U.S. Pat. No. 4,962,188; Uhr et al., U.S. Pat. No. 4,792,447; Masuho et al., U.S. Pat. Nos. 4,450,154 and 4,350,626. These agents include a cell-targeting moiety, such as a growth factor or an antigen-binding protein, linked to a plant or bacterial toxin. They kill cells by mechanisms different from conventional chemotherapy, thus potentially reducing or eliminating cross resistance to conventional chemotherapeutic agents.

Copending U.S. patent application Ser. No. 08/305,770, filed Sep. 13, 1994, describes compositions and methods for specific intracellular delivery of a chemical agent into a CR2-receptor-bearing cell, e.g. B lymphocytes. The compositions comprise a CR2-receptor-binding and endocytosis-inducing ligand (CBEL) coupled to the chemical agent. The CBEL binds to the CR2 receptor on the surface of B lymphocytes and elicits endocytosis of the composition such that the composition is transported to lysosomes. In the lysosomes, the chemical agent is preferably separated from the remainder of the composition such that the chemical agent can be transported or diffuse into the cytoplasm or nucleus. Optionally, the composition can include a spacer, which can be either biodegradable (in the lysosome) or non- biodegradable, for coupling the CBEL to the chemical agent. Chemical agents can include cytotoxins, transforming nucleic acids, gene regulators, labels, antigens, drugs, and the like. The composition can further comprise a carrier such as another water soluble polymer, liposome, or particulate.

Copending U.S. patent applications Ser. No. 08/616,693, filed Mar. 15, 1996, now abandoned, and Ser. No. 08/857,009, now abandoned, filed May 15, 1997, describe compositions and methods for specific intracellular delivery of a chemical agent into T lymphocytes. The compositions are represented by the formula $[L-S]_a-C-[S-A]_b$, wherein L is a ligand configured for binding to a receptor on a T lymphocyte and stimulating receptor-mediated endocytosis of the composition, A is a chemical agent, S is a spacer moiety, C is a water soluble polymer having functional groups compatible with forming covalent bonds with the ligand, chemical agent, and spacer, and a and b are positive integers. These compositions are also designed to be transported to lysosomes, where the chemical agent is separated from the remainder of the composition for diffusion or transport to other locations in the cell. Preferred water soluble polymers include poly(ethylene glycol) and a copolymer of N-(2-hydroxypropyl)methacrylamide (HPMA). Preferred chemical agents include cytotoxins, transforming nucleic acids, gene regulators, labels, antigens, drugs, and the like. The composition can further comprise a carrier such as other water soluble polymers, liposomes, or particulates.

It would also be advantageous to develop additional compositions that are specifically targeted to other receptors on T lymphocytes. For example, targeting of T lymphocytes would enable therapeutic applications for T-cell-associated diseases and tissue graft rejection. Such T-cell-associated diseases include arthritis, T-cell lymphoma, skin cancers, psoriasis, multiple sclerosis, Type II diabetes mellitus, and diseases resulting from HIV infection.

In view of the foregoing, it will be appreciated that compositions for intracellular delivery of chemical agents to T cells and methods of use thereof would be significant advancements in the art.

BRIEF SUMMARY OF THE INVENTION

It is an object of the present invention to provide compositions for intracellular delivery of selected chemical agents to a specific cell type, i.e. IL-2-receptor-bearing cells.

It is also an object of the invention to provide methods of making and methods of using compositions for delivery of selected chemical agents into IL-2-receptor-bearing cells.

It is another object of the invention to provide compositions and methods for delivering selected chemical agents into IL2-receptor-bearing cells using water soluble polymers that are inexpensive, FDA-approved, and resistant to development of an antibody response.

It is yet another object of the invention to provide compositions and methods of use thereof for delivery of selected chemical agents into activated T cells.

It is still another object of the invention to providing compositions and methods of use thereof for detecting a disease associated with elevated levels of soluble IL-2 receptor in body fluids, such as serum.

These and other objects are achieved by providing a composition for delivery of a chemical agent into an IL-2-receptor bearing cell, the composition comprising (a) a water-soluble, biocompatible polymer, (b) the chemical agent covalently, releasably coupled to the polymer, and (c) a ligand comprising an IL-2-receptor-binding peptide covalently coupled to the polymer.

In a preferred embodiment of the invention, the composition has a formula selected from the group consisting of $P-[T_a-L-S-A]_c$ and $[A-S]_d-P-[T_a-L]_c$, wherein L is the ligand; A is the chemical agent; S and T are spacers, wherein at least S is biodegradable and S and T can be the same or different; P is the water soluble polymer having functional groups compatible with forming covalent bonds with the ligand; a is 0 or 1; and c and d are integers of at least 1.

Preferably, P is a polyalkylene oxide. Preferred polyalkylene oxides are selected from the group consisting of alpha-substituted polyalkylene oxide derivatives, polyethylene glycol (PEG) homopolymers and derivatives thereof, polypropylene glycol homopolymers and derivatives thereof, alkyl-capped polyethylene oxides, bis-polyethylene oxides, copolymers of poly(alkylene oxides), and block copolymers of poly(alkylene oxides) or activated derivatives thereof. Preferably, the polyalkylene oxide has a molecular weight of about 200 to about 50,000. More preferably, the polyalkylene oxide has a molecular weight of about 2,000 to about 20,000. Most preferably, the polyalkylene oxide has a molecular weight of about 20,000. Especially preferred polyalkylene oxides are polyethylene glycol and polyethylene oxide.

The IL-2-receptor-binding peptide is preferably a member selected from the group consisting of SEQ ID NO:1 and biologically functional equivalents thereof. More preferably, the IL-2-receptor-binding peptide is a member selected from the group consisting of SEQ ID NO: 1 through SEQ ID NO: 11, and SEQ ID NO:24 through SEQ ID NO:47.

The chemical agent is preferably selected from the group consisting of cytotoxins, transforming nucleic acids, gene regulators, labels, antigens, and drugs.

Preferably, the spacer comprises a peptide. A preferred peptide spacer comprises Gly-Phe-Leu-Gly (SEQ ID NO:21).

In one preferred embodiment, the composition further comprises a carrier selected from the group consisting of other water soluble polymers, liposomes, and particulates. Preferably, such water soluble polymers are selected from the group consisting of dextran, inulin, poly(L-lysine) with modified epsilon amino groups, poly(L-glutamic acid), and N-substituted methacrylamide-containing polymers and copolymers.

A method of delivering a chemical agent in vitro into an IL-2-receptor-bearing cell in a population of cells comprises the steps of:
  (a) providing a composition comprising (i) a water-soluble, biocompatible polymer, (ii) the chemical agent covalently, releasably coupled to the polymer, and (iii) a ligand comprising an IL-2-receptor-binding peptide covalently coupled to the polymer; and
  (b) contacting the population of cells with an effective amount of the composition under conditions wherein the ligand binds to an IL-2 receptor on the IL-2-receptor-bearing cell and elicits endocytosis of the composition.

A method of delivering a chemical agent into an IL-2-receptor-bearing cell in a warm-blooded animal, comprises the steps of:
  (a) providing a composition comprising (i) a water-soluble, biocompatible polymer, (ii) the chemical agent covalently, releasably coupled to the polymer, and (iii) a ligand comprising an IL-2-receptor-binding peptide covalently coupled to the polymer; and
  (b) systemically administering to the warm-blooded animal an effective amount of the composition under conditions wherein the ligand contacts and binds to an IL-2 receptor on the IL-2-receptor-bearing cell and elicits endocytosis of the composition.

Another aspect of the invention relates to a composition comprising a peptide selected from the group consisting of SEQ ID NO:2 through SEQ ID NO: 11 and SEQ ID NO:22 through SEQ ID NO:47 and amides thereof.

A method for detecting a disease associated with elevated levels of soluble interleukin-2 receptor in circulation comprises the steps of:
  (a) providing a composition comprising an IL-2-receptor-binding peptide;
  (b) mixing the composition with a body fluid to be tested under conditions suitable for binding of the composition to said soluble interleukin-2 receptor in the body fluid to form a complex; and
  (c) detecting the complex and determining whether the complex is present at elevated levels as compared to normal individuals.

Diseases that can be detected according to this method include T-cell lymphocytic leukemia, T-cell acute lymphoblastic leukemia, peripheral T-cell lymphoma, Hodgkin's disease, and non-Hodgkin's lymphoma. Preferably, the body fluid that is tested is serum. Detection of the complex of peptide and soluble interleukin-2 receptor preferably comprises an enzyme-linked or radio-linked sorbent assay. IL-2 receptor-binding peptides that are suitable for this process include SEQ ID NO: 1 through SEQ ID NO: 11 and SEQ ID NO:22 through SEQ ID NO:47 and amides thereof. Especially preferred peptides are SEQ ID NO:27 and the amide thereof. As is well known in the art, such an amide is generally formed by reaction of an acid chloride of the peptide with ammonia, resulting in replacement of the -OH group of the C-terminal carboxylic acid with -NH$_2$.

DETAILED DESCRIPTION

Figure 1:
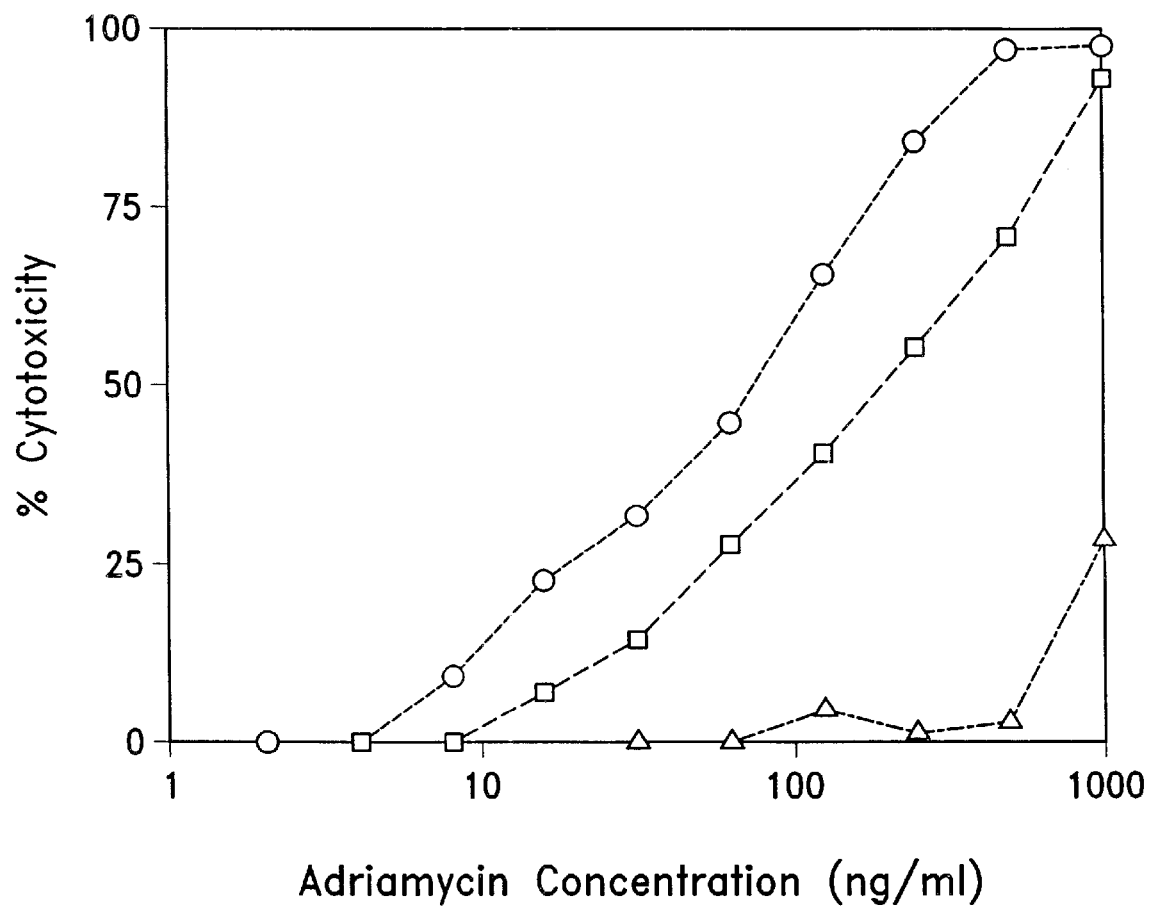
FIG. 1 shows the in vitro cytotoxic activity of a composition according to the present invention and control compositions against mouse CTIL-2 cells: (□) PEG-TT23-ADR (SEQ ID NO:22); (Δ) PEG-GFLG-ADR (SEQ ID NO:21); and (○) unconjugated adriamycin.

Before the present compositions and methods for targeted delivery into IL-2-receptor-bearing cells are disclosed and described, it is to be understood that this invention is not limited to the particular embodiments, process steps, and materials disclosed herein as such embodiments, process steps, and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition containing "a ligand" includes reference to two or more ligands, reference to "a chemical agent" includes reference to one or more of such chemical agents that may be the same or different chemical agents, and reference to "a spacer" includes reference to two or more spacers.

In describing and claiming the present invention, the following terminology will be used in accordance with the definitions set out below.

As used herein, "peptide" means peptides of any length and includes proteins. The terms "polypeptide" and "oligopeptide" are used herein without any particular intended size limitation, unless a particular size is otherwise stated.

As used herein, "IL-2-receptor-binding peptide" means a peptide configured for binding to an IL-2 receptor and stimulating internalization thereof by receptor-mediated endocytosis. According to the present invention, ligands comprising such IL-2-receptor-binding peptides are coupled to various functional molecules so that upon endocytosis of the ligands the various functional molecules coupled thereto are also internalized by the cells.

Preferred IL-2-receptor-binding peptides include the peptide having the amino acid sequence identified as SEQ ID NO:1 and biologically functional equivalents thereof. Such functional equivalents retain functionality in binding the IL2 receptor and eliciting receptor-mediated endocytosis although they may be truncations, deletion variants, or substitution variants of SEQ ID NO:1 or include additional amino acid residues attached thereto. It is also preferred that the IL-2-receptor-binding peptides have a size of about 6–20 amino acid residues, more preferably about 6–12 amino acid residues, and most preferably about 6–8 amino acid residues. More preferred IL-2 receptor binding peptides include SEQ ID NO:1 through SEQ ID NO:11 and SEQ ID NO:24 through SEQ ID NO:47. An especially preferred IL-2 receptor binding peptide is SEQ ID NO:27.

As mentioned above, changes may be made in the structure of the IL-2 receptor-binding peptide while maintaining the desirable receptor-binding characteristics. For example, certain amino acid residues may be substituted for other amino acid residues in a protein structure without appreciable loss of interactive binding capacity with structures such as, for example, antigen-binding regions of antibodies or binding sites of ligands such as an IL-2 receptor-binding peptide. Since it is the interactive capacity and nature of a protein that defines that protein's biological functional activity, certain amino acid sequence substitutions can be made in a protein's amino acid sequence and nevertheless obtain a protein with like properties. It is thus contemplated that various changes may be made in the sequence of an IL-2 receptor-binding peptide without appreciable loss of its biological utility or activity.

It is also well understood by the skilled artisan that inherent in the definition of a biologically functional equivalent protein or peptide is the concept that there is a limit to the number of changes that may be made within a defined portion of the molecule and still result in a molecule with an acceptable level of equivalent biological activity. It is also well understood that where certain residues are shown to be particularly important to the biological or structural properties of a protein or peptide, e.g. residues in active sites, such residues may not generally be exchanged.

Amino acid substitutions are generally based on the relative similarity of the amino acid side-chains relative to, for example, their hydrophobicity, hydrophilicity, charge, size, and the like. An analysis of the size, shape, and type of the amino acid side-chains reveals, for example, that arginine, lysine, and histidine are all positively charged residues; that alanine, glycine, threonine, and serine are all a similar size; and that phenylalanine, tryptophan, and tyrosine all have a generally similar shape. Therefore, based upon these considerations, the following conservative substitution groups or biologically functional equivalents have been defined:(a) Cys; (b) Phe, Trp, Tyr; (c) Gln, Glu, Asn, Asp; (d) His, Lys, Arg; (e) Ala, Gly, Pro, Ser, Thr; and (f) Met, Ile, Leu, Val. M. Dayhoff et al., Atlas of Protein Sequence and Structure (Nat'l Biomed. Res. Found., Washington, D.C., 1978), hereby incorporated by reference.

To effect more quantitative changes, the hydropathic index of amino acids may be considered. Each amino acid has been assigned a hydropathic index on the basis of its hydrophobicity and charge characteristics, which are as follows: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art. J. Kyte & R. Doolittle, A simple method for displaying the hydropathic character of a protein, 157 J. Mol. Biol. 105–132 (1982), incorporated herein by reference. It is known that certain amino acids may be substituted for other amino acids having a similar hydropathic index or score and still retain a similar biological activity. In making changes based on the hydropathic index, the substitution of amino acids whose hydropathic indices are within ±2 is preferred, within ±1 is particularly preferred, and within ±0.5 is even more particularly preferred.

It is also understood that an amino acid can be substituted for another having a similar hydrophilicity value and still obtain a biologically equivalent protein. As detailed in U.S. Pat. No. 4,554,101, the following hydrophilicity values have been assigned to amino acid residues: arginine (±3.0); lysine (±3.0); aspartate (±3.0); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (-1.8); tyrosine (−2.3); phenylalanine (−2.5); tryptophan (−3.4).

In making changes based upon similar hydrophilicity values, the substitution of amino acids whose hydrophilicity values are within ±2 is preferred, within ±1 is particularly preferred, and within ±0.5 is even more particularly preferred.

A hexapeptide believed to be a part of IL-2 that binds to the IL-2 receptor has been identified (SEQ ID NO: 1), D. A. Weigent et al., 139 Biochem. Biophys. Res. Commun. 367–74 (1986). Moreover, regions of homology between this IL-2 hexapeptide and env proteins of immunosuppressive retroviruses have been discovered. D. A. Weigent et al., supra; W. E. Reiher III et al., 83 Proc. Nat'l Acad. Sci. USA 9188–92 (1986). Thus, amino acid substitutions in these regions of homology as compared to the IL2 hexapeptide may be considered to be biologically functional equivalents. Therefore, illustrative biologically functional equivalents of SEQ ID NO:1 include SEQ ID NO:2 through SEQ ID NO:6. Other illustrative biologically functional equivalents have also been discovered, including SEQ ID NO:7 through SEQ ID NO:11, and SEQ ID NO:22 through SEQ ID NO:47. Additional biologically functional equivalents can be discovered by a person of ordinary skill in the art according to the guidance and principles disclosed herein without undue experimentation. For example, the peptides of SEQ ID NO: 1 through SEQ ID NO:6 are fairly hydrophobic. It has been determined that adding selected amino acid residues, such glycine and/or threonine, to the amino terminus results in improved water solubility of such peptides while preserving activity.

As used herein, "macromolecule" means a composition comprising a water soluble polymer with a ligand and a chemical agent bound thereto. Preferably the polymer is a polyalkylene oxide and the ligand is an oligopeptide. The chemical agent can be from many different classes of molecules, as explained in more detail herein.

As used herein, "prodrug" means a chemical agent that is chemically modified to overcome a biological barrier. When a chemical agent is converted into its prodrug form, its biological activity is eliminated or substantially reduced, but the biological barrier that inhibited its effectiveness is no longer problematic. The chemical group that is attached to the chemical agent to form the prodrug, i.e. the "promoiety", is removed from the prodrug by enzymatic or nonenzymatic means to release the active form of the chemical agent. See A. Albert, Chemical Aspects of Selective Toxicity, 182 Nature 421 (1958). The instant compositions are prodrugs because the chemical agent that has the selected effect when internalized in IL-2-receptor-bearing cells is modified with a ligand, water soluble polymer, and, optionally, spacers such that the composition is delivered into the IL-2-receptor-bearing cells, thus penetrating the cell membrane thereof. The biological effect of the chemical agent is greatly reduced or eliminated until the composition is delivered into the cell and the chemical agent is released from the remainder of the composition by biodegradation of the spacer.

As used herein, "chemical agent" means and includes any substance that has a selected effect when internalized into an IL-2-receptor-bearing cell. Certain chemical agents have a physiological effect, such as a cytotoxic effect or an effect on gene regulation, when internalized into the cell. A "transforming nucleic acid" (RNA or DNA), when internalized into a cell, can be replicated and/or expressed within the cell. Other nucleic acids can interact with regulatory sequences or regulatory factors within the cell to influence gene expression within the cell in a selected manner. A detectable label delivered into cells can permit identification of cells that have internalized the compositions of the present invention by detection of the label. Drugs or pharmacologically active compounds can be used to ameliorate pathogenic effects or other types of disorders. Particularly useful chemical agents include polypeptides, and some such chemical agents are active fragments of biologically active proteins, or are specific antigenic fragments (e.g., epitopes) of antigenic proteins. Thus, chemical agents include cytotoxins, gene regulators, transforming nucleic acids, labels, antigens, drugs, and the like.

As used herein, "drug" or "pharmacologically active agent" means any chemical material or compound suitable for intracellular administration in a IL-2 receptor bearing cell, e.g. an activated T lymphocyte, that stimulates a desired biological or pharmacological effect in such cell.

As used herein, "carrier" means water soluble polymers, particulates, or liposomes to which a composition according to the instant invention can be coupled. Such carriers increase the molecular size of the compositions and may provide added selectivity and/or stability. Such selectivity arises because carrier-containing compositions are too large to enter cells by passive diffusion, and thus are limited to entering cells through receptor-mediated endocytosis. The potential for use of such carriers for targeted drug delivery has been established. See, e.g., J. Kopecek, 5 Biomaterials 19 (1984); E. Schacht et al., Polysaccharides as Drug Carriers, in Controlled-Release Technology 188 (P. I. Lee & W. R. Good, eds., 1987); F. Hudecz et al., Carrier design: Cytotoxicity and Immunogenicity of Synthetic Branched Polypeptides with Poly(L-lysine) Backbone, 19 J. Controlled Release 231 (1992); Z. Brich et al., Preparation and Characterization of a Water Soluble Dextran Immunoconjugate of Doxorubicin and the Monoclonal Antibody (ABL364), 19 J. Controlled Release 245 (1992). Thus, illustrative water soluble polymers include dextran, inulin, poly(L-lysine) with modified epsilon-amino groups, poly(L-glutamic acid), polymers and copolymers of N-substituted methacrylamide, and the like.

As used herein, "effective amount" is an amount sufficient to produce a selected effect. For example, a selected effect of a composition containing a cytotoxin as the chemical agent could be to kill a selected proportion of IL-2-receptor-bearing cells, e.g. activated T cells, within a selected time period. An effective amount of the composition would be the amount that achieves this selected result, and such an amount could be determined as a matter of routine by a person skilled in the art.

The compositions of the present invention provide intracellular delivery of a chemical agent capable of eliciting a selected effect when delivered into an IL-2-receptor-bearing cell. Illustrative embodiments of the composition have a formula selected from the group consisting of P—[$T_a$—L—$S_b$—A]$_c$ and [A—$S_b$]$_d$—P—[$T_a$—L]$_c$, wherein L is a ligand configured for binding to an IL-2 receptor on the IL-2-receptor-bearing cell and stimulating receptor-mediated endocytosis of the composition; A is the chemical agent; S and T are spacers, wherein at least S is biodegradable; P is a water soluble polymer having functional groups compatible with forming covalent bonds with the ligand; a and b are integers of 0 or 1; c is an integer of at least 1; and d is an integer of at least 1. Preferably, c is an integer of 2 to about 1000.

The spacers are preferably biodegradable such that the chemical agent is detached from the composition by hydrolysis and/or enzymatic cleavage inside IL-2-receptor-bearing cells, e.g. T cells, especially in lysosomes. Once detached, the chemical agent diffuses or is transported to other locations in the cell where it can exert its functional effect in the cell. Illustrative of such spacers is the peptide Gly-Phe-Leu-Gly (SEQ ID NO:21). Equivalent peptide spacers are well known in the art.

The chemical agent is selected from the group consisting of cytotoxins, transforming nucleic acids, gene regulators, labels, antigens, drugs, and the like.

The water soluble polymer (represented by P in the formula above) is preferably a poly(alkylene oxide). Within this group of substances are alpha-substituted polyalkylene oxide derivatives, such as methoxypolyethylene glycols or other suitable alkyl-substituted derivatives, such as those containing $C_1$–$C_4$ alkyl groups. Preferably the polymer is a monomethyl-substituted PEG homopolymer. Other poly (alkylene oxides) are also useful, including other polyethylene glycol (PEG) homopolymers and derivatives thereof, polypropylene glycol homopolymers and derivatives thereof, other alkyl-capped polyethylene oxides, bis-polyethylene oxides, copolymers of poly(alkylene oxides), and block copolymers of poly(alkylene oxides) or activated derivatives thereof. Other preferred PEGs include branched and star PEGs, such as are commercially available from Shearwater Polymers, Inc. (Huntsville, Ala.). Y. Gnanou et al., 189 Makromol. Chem. 2885 (1988); D. Rein et al., 44 Acta Polymer. 225 (1993);. E. W. Merrill, U.S. Pat. No. 5,171,264; hereby incorporated by reference. In those aspects of the invention where PEG-based polymers are used, it is preferred that they have molecular weights of from about 200 to about 50,000. Molecular weights of about 2,000 to about 20,000 are preferred, and molecular weights of about 20,000 are particularly preferred. PEG is preferred because it is inexpensive, approved by the FDA for administration to humans, and is resistant to eliciting an antibody response. Poly(ethylene oxide) (PEO) is another preferred water soluble polymer represented by P. The coupling of a ligand to a chemical agent can be, without limitation, by covalent bond, electrostatic interaction, hydrophobic interaction, physical encapsulation, and the like.

The compositions of the present invention can further comprise a carrier selected from the group consisting of other water soluble polymers, liposomes, and particulates. Such water soluble polymers for use as carriers are selected from the group consisting of dextran, inulin, poly(L-lysine) (PLL) with modified epsilon amino groups, poly(L-glutamic acid) (PGA), polymers and copolymers of N-substituted methacrylamide, and the like. A preferred water soluble polymer is a copolymer of N-(2-hydroxypropyl) methacrylamide (HPMA).

Thus, according to the invention, the composition provides means for preferential binding to an IL-2 receptor, such as on activated T cells, thus triggering internalization of the composition by endocytosis. The chemical agent provides means for achieving a selected effect in the IL2-receptor bearing cells. Accordingly, for example, chemical agents comprise cytotoxins, including radionuclides, for selective killing or disabling of cells; nucleic acids for genetically transforming or regulating gene expression in cells; drugs or other pharmacologically active agents for achieving a selected therapeutic effect; labels, including fluorescent, radioactive, and magnetic labels, for permitting detection of cells that have taken up the compositions; and the like.

IL-2 is a lymphocyte growth factor produced by T cells that is essential for a normal immune response. Binding of IL-2 to the IL-2 receptor precedes internalization by receptor-mediated endocytosis. The human IL-2 gene has been sequenced, T. Taniguchi et al., 302 Nature 305–10 (1983), hereby incorporated by reference, as has the gene for the human IL-2 receptor, W. J. Leonard et al., 311 Nature 626–31 (1984); T. Nikaido et al., 311 Nature 631–35 (1984); D. Cosman et al., 312 Nature 768–71 (1984). The IL-2 receptor is a heterotrimeric glycoprotein complex on the cell membrane with a 55 kDa α subunit, a 75 kDa β subunit, and a 64 kDa γ subunit. The only normal human tissues expressing the α and β subunits are activated T cells, B cells, LGL cells, and monocytes and some liver Kupffer cells, macrophages, and skin Langerhans' cells. A. E. Frankel et al., 11 Leukemia 22–30 (1997). A variety of hematologic neoplasms may show high affinity IL-2 receptor expression including hairy cell leukemia, adult T cell leukemia, and a fraction of cutaneous T cell lymphomas and B cell chronic lymphocytic leukemias. Recombinant toxins targeted to the IL-2 receptor have been described wherein the ligand is IL-2. A. E. Frankel et al., supra; U.S. Pat. No. 4,675,382; J. vanderSpek et al., 268 J. Biol. Chem. 12077–82 (1993); I. Pastan & D. FitzGerald, supra.

In some embodiments of the present invention, the compositions are constructed by chemically conjugating the ligand and chemical agent to the water soluble polymer. "Chemically conjugating" the ligand and the chemical agent to the water soluble polymer, as that term is used herein, means covalently bonding the ligand and chemical agent to each other, preferably by way of a spacer moiety, and conjugating the resulting ligand/agent conjugate to the water soluble polymer. In particular embodiments, a spacer moiety is used to form a linkage between the ligand and the chemical agent.

Peptide portions of the compositions of the present invention can be produced in a genetically engineered organism, such as *E. coli*, as a "fusion protein." That is, a hybrid gene containing a sequence of nucleotides encoding a ligand, spacer, or peptide chemical agent can be constructed by recombinant DNA technology. This hybrid gene can be inserted into an organism such that the "fusion protein" encoded by the hybrid gene is expressed. The fusion protein can then be purified by standard methods, including affinity chromatography. Peptides containing a ligand, spacer, or peptide chemical agent can also be constructed by chemical synthesis. Short peptide ligands are generally preferred, both because short peptides can be manipulated more readily and because the presence of additional amino acids residues, and particularly of substantial numbers of additional amino acids residues, may interfere with the function of the peptide ligand in stimulating internalization of the chemical agent by endocytosis.

Compositions according to the present invention preferably also further include a protease digestion site, preferably in the spacer moiety, situated such that once the composition is within the cell, such as in a lysosome, the chemical agent can be separated from the remainder of the composition by proteolysis of the digestion site. Such a protease susceptible spacer can be added regardless of whether the peptide portions of the composition are synthesized chemically or as expression peptides in a genetically engineered organism. In the latter case, nucleotides encoding the protease susceptible spacer can be inserted into the hybrid gene encoding the ligand and or a peptide chemical agent by techniques well known in the art. In one illustrative embodiment, the protease-susceptible spacer is designed to be cleaved by proteolysis in the lysosome of the target cell. The composition that is internalized by endocytosis is packaged in an endocytic vesicle, which is transported to a lysosome. Once in the lysosome, the protease-susceptible spacer is cleaved, and the chemical agent is then available to be transported to the cytoplasm.

Another aspect of the present invention features a method for specifically effecting a desired activity in IL-2-receptor-bearing cells, e.g. activated T lymphocytes, contained in a heterogeneous population of cells, by the step of contacting the population of cells with a composition, prepared according to the present invention, that directs such activity into the cells. The compositions of the invention are selectively bound to IL-2-receptor-bearing T cells in the mixed population, whereupon endocytosis of the composition into such activated T cells is stimulated, and the chemical agent effects its activity within such T cells.

This application employs, except where otherwise indicated, standard techniques for manipulation of peptides and for manipulation of nucleic acids for expression of peptides. Techniques for conjugation of oligopeptides and oligonucleotides are known in the art, and are described for example in T. Zhu et al., 3 Antisense Res. Dev. 265 (1993); T. Zhu et al., 89 Proc. Nat'l Acad. Sci. USA 7934 (1992); P. Rigaudy et al., 49 Cancer Res. 1836 (1989), which are hereby incorporated by reference.

As is noted above, the invention features peptides, employed as ligands, spacers, and/or chemical agents. The peptides according to the invention can be made by any of a variety of techniques, including organic synthesis and recombinant DNA methods. Techniques for chemical synthesis of peptides are described, for example, in B. Merrifield et al., 21 Biochemistry 5020 (1982); Houghten, 82 Proc. Nat'l Acad. Sci. USA 5131 (1985); M. Bodanszky & A. Bodanszky, The Practice of Peptide Synthesis (Springer-Verlag 2d ed., 1994), incorporated herein by reference. Techniques for chemical conjugation of peptides with other molecules are known in the art.

A fusion protein according to the invention can be made by expression in a suitable host cell of a nucleic acid containing an oligonucleotide encoding a ligand and/or spacer and/or chemical agent. Such techniques for producing recombinant fusion proteins are well-known in the art, and are described generally in, e.g., J. Sambrook et al., Molecular Cloning: A Laboratory Manual (2d ed., 1989), the pertinent parts of which are hereby incorporated herein by reference. Reagents useful in applying such techniques, such as restriction endonucleases and the like, are widely known in the art and commercially available from any of several vendors.

Construction of compositions according to the present invention will now be described, with particular reference to examples in which a peptide ligand coupled to a biodegradable spacer (SEQ ID NO:21) and a cytotoxic chemical agent, adriamycin, are coupled to PEG.

EXAMPLE 1

In this example, 7.8 g of branched, 8-arm PEG-COOH (20 kDa; Shearwater Polymers, Inc., Huntsville, Ala.) and 0.25 g of p-nitrophenol were dissolved in 500 ml of anhydrous tetrahydrofuran (THF), making the solution 3.6 mM with respect to the p-nitrophenol. The solution was cooled in an ice bath, and 0.9341 g of dicyclohexylcarbodiimide (DCC, Sigma) in THF was added to the reaction mixture in 4 aliquots. The reaction solution was stirred for 45 minutes in the ice bath. The temperature of the reaction solution was then raised to room temperature, and the reaction was continued for 101 hours. The reaction solution was then filtered through filter paper, and the filtrate was concentrated by evaporation of the solvent with a rotary evaporator using a water pump. The clear concentrated solution (30 ml) was added to ether (750 ml). The precipitate was filtered, washed in ether, and dried in air. An aliquot of the product was dissolved in 0.1 NaOH, and concentration of the liberated p-nitrophenol was estimated by spectrophotometry at 400 nm using a molar extinction coefficient of $\epsilon=1.8\times10^4$ 1/mol-cm. The product, PEG-ONp, was determined to have an ONp content of 201.3 $\mu$mol/g.

PEG-ONp (0.1628 g, ONp content of 201.3 $\mu$mol), prepared as described above, was dissolved in 2 ml anhydrous dimethylformamide (DMF), and 42.4 mg of peptide TT23 (SEQ ID NO:22) was added to the solution. About 150 $\mu$l of triethylamine diluted 1:2 with DMF was added to the reaction mixture three times at 15 minute intervals, and then the solution was stirred for 19 hours at room temperature. Next, the reaction solution was added to cold ether (300 ml), and the conjugate precipitates were filtered, washed with 200 ml of ether, and dried. Amino acid analysis of the conjugate, PEG-T23-OH, showed 1 mole of peptide TT23 incorporated per mole of PEG.

Adriamycin (7.6 mg, Sigma) and PEG-TT23-OH (85 mg) were dissolved in 2 ml DMF, and solid DCC (14 mg) was added to the solution. The reaction was carried out for 17 hours, precipitated with 200 ml ether, filtered, and washed with ether. The precipitate was dried under vacuum and then dissolved in PBS buffer. The solution was dialyzed for 25 hours with 3 changes of PBS buffer. Adriamycin content of the product, PEG-TT23-ADR, was determined by spectrophotometry at 490 nm.

EXAMPLE 2

A control composition having the formula PEG-Gly-Phe-Leu-Gly-ADR (hereinafter, "PEG-GFLG-ADR;" SEQ ID NO:21) was prepared according to the procedure of Example 1.

EXAMPLE 3

A composition having the formula PEG-Gly-Leu-Glu-Arg-Ile-Leu-Leu-Gly-Phe-Leu-Gly-Adriamycin (hereinafter, "PEG-TT7-ADR;" SEQ ID NO:14) was prepared according to the procedure of Example 1.

EXAMPLE 4

A composition having the formula PEG-Gly-Leu-Glu-His-Ile-Leu-Leu-Gly-Phe-leu-Gly-Adriamycin (SEQ ID NO: 15) was prepared according to the procedure of Example 1.

EXAMPLE 5

A composition having the formula PEG-Gly-leu-Gln-His-Ile-Leu-Leu-Gly-Phe-Leu-Gly-Adriamycin (SEQ ID NO: 16) was prepared according to the procedure of Example 1.

EXAMPLE 6

A composition having the formula PEG-Gly-leu-Asp-His-Ile-Phe-Leu-Gly-Phe-leu-Gly-Adriamycin (SEQ ID NO: 17) is prepared according to the procedure of Example 1.

EXAMPLE 7

A composition having the formula PEG-Gly-Leu-Asn-His-Ile-Phe-Leu-Gly-Phe-Leu-Gly-Adriamycin (SEQ ID NO:18) is prepared according to the procedure of Example 1.

EXAMPLE 8

A composition having the formula PEG-Thr-Gly-Leu-Gln-His-Ile-Leu-Leu-Gly-Phe-Leu-Gly-Adriamycin (hereinafter, "PEG-TT15-ADR"; SEQ ID NO:19) was prepared according to the procedure of Example 1.

EXAMPLE 9

A composition having the formula PEG-Ser-leu-Gln-His-Ile-Leu-Leu-Gly-Phe-Leu-Gly-Adriamycin (SEQ ID NO:20) is prepared according to the procedure of Example 1.

EXAMPLE 10

A composition having the formula PEG-Gly-leu-Gln-His-leu-Phe-Leu-Gly-Adriamycin (hereinafter, "PEG-TT1 3-ADR"; SEQ ID NO:13) was prepared according to the procedure of Example 1.

EXAMPLE 11

A composition having the formula PEG-Thr-Gly-Leu-Asp-Arg-Ile-Leu-Leu-Adriamycin (hereinafter, "PEG-TT27-ADR"; SEQ ID NO:24) is prepared according to the procedure of Example 1.

EXAMPLE 12

A composition having the formula PEG-Thr-Gly-Leu-Asp-Arg-Leu-Leu-Leu-Adriamycin (SEQ ID NO:25) is prepared according to the procedure of Example 1.

EXAMPLE 13

A composition having the formula PEG-Thr-Gly-Leu-Asn-Arg-Leu-Leu-Leu-Adriamycin (SEQ ID NO:26) is prepared according to the procedure of Example 1.

EXAMPLE 14

A composition having the formula PEG-Thr-Gly-leu-Asn-Arg-Ile-Leu-Leu-Adriamycin (SEQ ID NO:27) is prepared according to the procedure of Example 1.

EXAMPLE 15

A composition having the formula PEG-Thr-Gly-Leu-Asp-Arg-Ile-Phe-Leu-Gly-Adriamycin (SEQ ID NO:28) is prepared according to the procedure of Example 1.

EXAMPLE 16

A composition having the formula PEG-Thr-Gly-Leu-Asp-Arg-Leu-Phe-Leu-Gly-Adriamycin (SEQ ID NO:29) is prepared according to the procedure of Example 1.

EXAMPLE 17

A composition having the formula PEG-Thr-Gly-Leu-Asn-Arg-Ile-Phe-Leu-Gly-Adriamycin (SEQ ID NO:30) is prepared according to the procedure of Example 1.

EXAMPLE 18

A composition having the formula PEG-Thr-Gly-Leu-Asn-Arg-Leu-Phe-Leu-Gly-Adriamycin (SEQ ID NO:31) is prepared according to the procedure of Example 1.

EXAMPLE 19

The in vitro effects of PEG-TT23-ADR prepared according to the procedure of Example 1, PEG-GFLG-ADR prepared according to the procedure of Example 2, and unconjugated adrianycin were tested on mouse CTLL2 cells (ATCC No. TIB214) as follows. CTLL-2 cells express the IL-2 high affinity receptor. Triplicate samples of $1 \times 10^5$ cells each were mixed with different concentrations of the purified compositions in 0.1 ml of culture medium (RPMI 1640, 10% fetal calf serum) in the wells of a 96-well microtiter plate (Falcon Microtest 111), and incubated for 48 hours at 37° C. in a humidified, 5% $CO_2$ atmosphere. Thereafter, cell viability was assessed by a colorimetric method using the tetrazolium compound MTS (3-(4,5-dimethylthiazol-2-yl)-5-(3-carboxymethoxyphenyl)-2-(4-sulfophenyl)-2H-tetrazolium, inner salt) and an electron coupling reagent, PMS (phenazine methosulfate). A. J. Cory et al., 3 Cancer Commun. 207 (1991); T. L. Riss & R. A. Moravec, 3 Mol. Biol. Cell. 184a (Supp.; 1992); T. M. Buttke et al., 157 J. Immunol. Methods 233 (1993), hereby incorporated by reference. MTS is bioreduced by living cells into a soluble formazan product. The absorbence of the formazan at 490 nm can be measured directly from 96 well assay plates without additional processing. The quantity of formazan product as measured by the absorbence at 490 nm is directly proportional to the number of living cells in culture. Reagents for the MTS assay were obtained from Promega Corp. (Madison, Wisconsin). According to this method, 20 µl of MTS/PMS solution (Promega No. G-5421) was added to each well of the assay plate. The plate was then further incubated at 37° C. in a humidified, 5% $CO_2$ atmosphere for 4 hours. The absorbence of each well was then measured at 490 nm with an EL311 Microplate Autoreader (Bio-Tek Instruments). The mean absorbence for each treatment was then calculated, and the percent cytotoxicity was determined using the formula:

$$\% \text{ cytotoxity} = \left(1 - \frac{A_S}{A_C}\right) \times 100$$

wherein $A_S$ represents the mean absorbence for each treatment and $A_C$ represents mean absorbence of the control treatment, i.e. cells not exposed to a conjugate.

FIG. 1 shows that PEG-TT23-ADR (□) kills such CTILL-2 T cells at concentrations much lower than that required for PEG-GFLG-ADR (Δ) to effect similar levels of cytotoxicity. These results show that the presence of a ligand specific for binding to the IL-2 receptor and inducing receptor-mediated endocytosis results in much greater cytotoxicity than a PEG- and adriamycin-containing conjugate lacking such ligand. Thus, a conjugate bearing an IL-2-receptor specific ligand is internalized with much greater efficiency that similar conjugates lacking such a ligand. The unconjugated adriamycin control (○) rapidly diffuses into the cells and kills them. As expected, the cytotoxicity from PEG-TT23-ADR requires higher concentrations of adriamycin than unconjugated adriamycin due to the requirement that PEG-TT23-ADR be internalized by endocytosis.

EXAMPLE 20

The in vitro effects of IL-2-receptor-targeted conjugates on IL-2-induced proliferation of murine splenocytes was examined.

A sterile splenocyte suspension was prepared as follows. Spleens were aseptically removed from male C57 BIJ6 mice and placed in sterile tissue culture medium (RPMI plus 10% fetal calf serum). The spleens were teased apart and gently aspirated using a Pasteur pipet. The resulting spleen cell suspension was then filtered through sterile gauze and centrifuged at 150×g for 10 minutes at 20° C. The supernate was discarded, and erythrocytes in the cell pellet were selectively lysed by resuspending the pellet in lysis buffer (155 mM $NH_4Cl$, 13.41 mM $KHCO_3$, and 100 mM EDTA in dH2O). After 30 seconds, an equal volume of tissue culture medium was added to the suspension to restore isotonicity. The cell suspension was again centrifuged at 150×g for 10 minutes at 20° C., and the resulting cell pellet was washed once using tissue culture medium. The washed cell pellet was finally resuspended in tissue culture medium, and cell density was adjusted to $5 \times 10^6$ cells/ml.

To the wells of a 96well assay plate (Falcon MICROTEST I), 50 µl volumes of the splenocyte suspension were added. Competitor (conjugate) solutions were prepared and diluted in tissue culture medium and added to the wells of the assay plate in 25 µl volumes. To control wells, 25 µl of tissue culture medium was added. The assay plate was then incubated for 60 minutes at 37° C. in a humidified atmosphere containing 5% $CO_2$ and 95% air. To the wells of the assay plate, 25 µl of either tissue culture medium or a solution containing recombinant human IL-2 (Pharmingen) at a concentration of 20 ng/ml (in tissue culture medium) was added. The assay plate was then incubated for 48 hours at 37° C. in a humidified atmosphere containing 5% $Co_2$ and 95% air.

Final results were quantitated as follows. Viable cell counts were performed for each separate well of the assay plate using the trypan blue exclusion method. Trypan blue is taken up and imparts a blue color to dead cells. Briefly, an aliquot of cells was twice diluted in 0.4% trypan blue stain (Sigma Chemical Co., St. Louis, Mo.) and incubated for 5 minutes before counting with a hemacytometer and an inverted microscope. The percentage of viable cells was calculated as the number of unstained cells per unit volume divided by the total number of stained and unstained cells× 100. Cell counts for each duplicate set of wells were averaged, and cell proliferation was calculated as percent change from control cells using the following formula:

$$\% \text{ Change} = \left[\frac{\text{mean cell count, test}}{\text{mean cell count, control}} - 1\right] \times 100$$

Percent inhibition of IL-2 induced proliferation was calculated as follows.

$$\% \text{ Inhibition} = \frac{[(\% \text{ Change}_{+IL-2}) - (\% \text{ Change}_{+IL-2+competitor})]}{\% \text{ Change}_{+IL-2}} \times 100$$

The materials tested in this example were PEG-TT23, prepared according to the procedure of Example 1 except that no adriamycin was conjugated thereto, and unconjugated peptide TT23.

Figure 2:
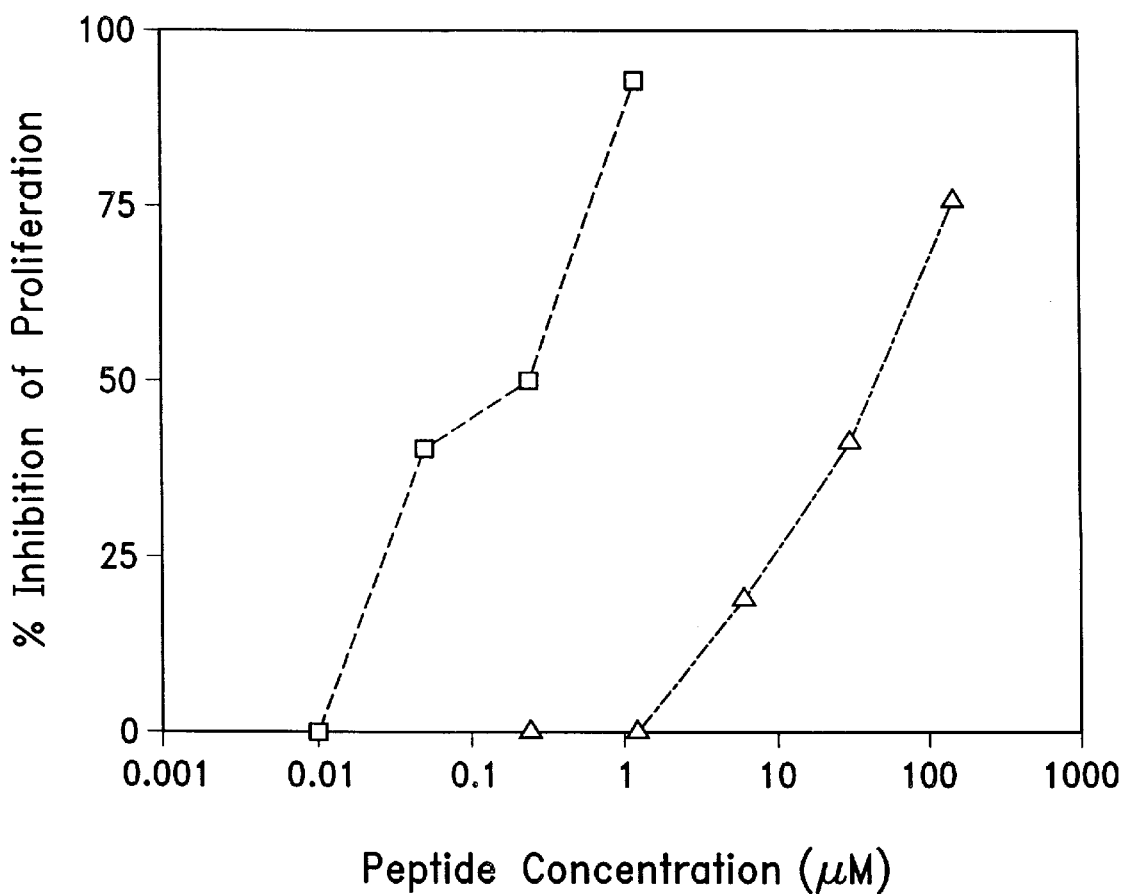
FIG. 2 shows the in vitro inhibition of IL-2-induced proliferation of murine splenocytes using (□) PEG-TT23 (SEQ ID NO:22) and (Δ) unconjugated peptide TT23 (SEQ ID NO:22)..

The results of conjugate inhibition of IL-2-induced proliferation of murine splenocytes with PEG-TT23-ADR and peptide TT23 are shown in FIG. 2. These results show that PEG-TT23 very effectively inhibits proliferation, whereas about 100-fold more unconjugated peptide TT23 is needed to achieve similar levels of inhibition. These results show that conjugate PEG-TT23 specifically binds to the IL-2 receptor.

The compositions according to the present invention can be employed for targeted delivery of a chemical agent to IL-2-receptor-bearing cells, e.g. activated T cells, generally by contacting the cells with the composition under conditions in which binding of the ligand to a receptor stimulates endocytosis of the composition into the cells. The chemical agent then acts on or within the targeted cell into which the composition is internalized, and the desired effect of the active agent can be confined to those cells having the receptor.

For example, a composition according to the invention can be employed as an effective antitumor agent in vivo for killing activated T cells. The composition can also be used for treating T-cell-associated diseases and tissue graft rejection. Such T-cell-associated diseases include arthritis, T-cell cancers such as cutaneous T-cell lymphoma, Hodgkin's disease, non-Hodgkin's lymphoma, skin cancers, psoriasis, graft rejection disease, multiple sclerosis, Type II diabetes mellitus, and diseases resulting from HIV infection. Preferably, the composition is administered to the subject by systemic administration, typically by subcutaneous, intramuscular, or intravenous injection, or intraperitoneal administration, which are methods well known in the art. Injectable preparations for such use can be made in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like may be added. Effective amounts of such compositions can be determined by those skilled in the art without undue experimentation according to the guidelines provided herein.

The composition can be contacted with the cells in vitro or in vivo. The T cells constitute a subpopulation of a mixed population of cell types; the ligand according to the invention can provide for endocytosis of the conjugate into T cells and possibly into a small proportion of other cells having a closely related receptor.

The chemical agent can have any of a variety of desired effects in the targeted cells. As mentioned above, in some particularly useful embodiments the chemical agent is effective on a cell only when, or principally when, the agent is internalized into the cell.

EXAMPLE 21
Treatment of Collagen-Induced Arthritis (CIA)

Collagen-induced arthritis (CIA) is a reliable model for pre-clinical testing of new immunomodulatory drugs for rheumatic diseases. CIA is induced in genetically susceptible mice by immunization with heterologous type II collagen (CII). The severity of CIA reflects the level of autoreactive T cells sensitized to CII, the production of CII-reactive autoantibody and the release in joint tissues of a variety of pro-inflammatory cytokines and chemokines. Treatment protocols that interfere with the T cell activation step inhibit CIA.

In this example, activated T cells were targeted with PEG-TT23-ADR, which has been shown to specifically bind to the IL-2 receptor (Example 20). The IL-2 receptor is only expressed by activated T cells. Thus, resting T cells are spared, and the intracellular toxic effects of the ADR-conjugate are directed to CII-reactive T cells.

B10.RIII mice were injected with CII (200 μg) emulsified with complete Freund's adjuvant (CFA; 200 μg H37Ra). At day 21, mice were boosted with 100 μg of CII, randomized for CIA severity (13/group), and an alternate day treatment protocol was begun. This secondary boost with CII is known to cause a rapid precipitation of arthritis onset. After such a secondary boost, B10.RIII mice show a very rapid onset of arthritis and very severe disease with a >90% incidence. Test groups received by i.p. injection: (A) PEG-TT23-ADR (2 mg/kg); (B) PEG-GFLG-ADR (2 mg/kg); (C) PBS (vehicle control). Mice were observed for 84 days for arthritis severity and weight changes.

Group B showed a significant weight loss of about 10%±8% as compared to Group C (about 5%±5%) $P \leq 0.04$, that was not evident in Group A mice (about 3%±6%) $P \leq 0.26$. Distribution curves of the cumulative daily arthritis scores revealed significant differences ($P \leq 0.02$) among the 3 groups. Importantly, Group A mice showed a significantly greater number of mice with only minimum arthritis as compared to the normally severe disease found in the majority of PBS control mice ($P \leq 0.02$).

Several potentially beneficial drugs for rheumatoid arthritis are contra-indicated by toxicity at required dosages. These data suggest that delivering a specific therapeutic agent only to the particular subset of lymphocytes directly involved in disease pathology may allow effective therapy to be accomplished at lower, more tolerable dosages.

EXAMPLE 22

A method of treating T cell lymphoma in a human comprises (a) providing a composition according to the present invention, such as PEG-TT23-ADR (SEQ ID NO:22), wherein the chemical agent is a cytotoxin, and (b) systemically administering an effective amount of the composition to an individual. An effective amount of the composition is systemically administered to the individual such that the composition enters the bloodstream and contacts T cells. The composition binds to an IL-2 receptor on the T cells and stimulates internalization of the composition by endocytosis. The biodegradable spacer is digested by intracellular proteases, releasing the adriamycin. The adriamycin then kills the cell by intercalating with DNA in the cell. This procedure reduces the number of malignant T cells in the body of the individual, thereby having a positive effect in treatment of the disease.

EXAMPLE 23

Alterations in the immune status of patients with various cancers results in release of soluble IL2 receptors (sIL-2R) in circulation. The sIL2R levels in T-cell lymphocytic leukemia, T-cell acute lymphoblastic leukemia, and peripheral T-cell lymphoma are an indication of the degree of T-cell or immune activation due to concomitant immunologic processes in these disorders. S. Raziuddin et al., 73 Cancer 2426–2431 (1994). Further, sIL-2R levels remain elevated in Hodgkin's disease and non-Hodgkin's lymphoma patients, even at the stage of minimal residual disease after intensive chemotherapy or radiotherapy. M. Kandefer-Szenrzen et al., 45 Arch. Immunol. Ther. Exp. (Warsz) 443–448 (1997). Therefore, detection of elevated levels of sIL-2R in circulation can be used as a diagnostic assay for such cancers.

In this example, compositions according to the present invention are used for detecting sIL-2R in circulation according to methods well known in the art. Peptides that bind to sIL-2R are used in modified ELISA or RIA assays for detecting such sIL-2R in circulation. The peptides are labeled with an enzyme or with a radiolabel. The labeled peptide is then mixed with a sample, such as a serum sample, and the mixture is incubated under conditions suitable for binding of the peptide to the sIL-2R to form a complex. This complex is then detected by colorimetric, fluorometric, radiometric, or similar assay. Elevated levels of circulating sIL-2R indicates the presence of cancer.

We claim:

1. A composition for delivery of a chemical agent into an IL2-receptor bearing cell, the composition comprising (a) a water-soluble, biocompatible polymer, (b) the chemical agent covalently, releasably coupled to the polymer, and (c) at least one copy of a ligand comprising an IL-2-receptor-binding peptide selected from the group consisting of SEQ ID NO:22 through SEQ ID NO:47, covalently coupled to the polymer.

2. The composition of claim 1 wherein said IL-2 receptor-binding peptide is SEQ. ID NO:27.

3. The composition of claim 1 wherein said chemical agent is selected from the group consisting of cytotoxins, transforming nucleic acids, gene regulators, labels, and antigens.

4. The composition of claim 3 wherein said chemical agent is a cytotoxin.

5. The composition of claim 4 wherein said cytotoxin is adriamycin.

6. The composition of claim 3 further comprising a carrier selected from the group consisting of other water soluble polymers, liposomes, and particulates.

7. The composition of claim 6 wherein said carrier is a water soluble polymer selected from the group consisting of dextran, inulin, poly(L-lysine) with modified epsilon amino groups, poly(L-glutamic acid), and polymers and copolymers of N-substituted methacrylamide.

8. The composition of claim 1 wherein said IL-2-receptor-bearing cell is an activated T cell.

9. A composition comprising (a) a water-soluble, biocompatible polymer, (b) a chemical agent, and (c) at least one copy of a ligand comprising an IL-2-receptor-binding peptide selected from the group consisting of SEQ ID NO:22 through SEQ ID NO:47, covalently coupled to the polymer;

wherein the composition has a formula selected from the group consisting of P—[$T_a$—L—S—A]$_c$ and [A—S]$_d$—P—[$T_a$—L]$_c$, wherein L is the ligand; A is the chemical agent; S and T are spacers, wherein at least S is biodegradable and S and T can be the same or different; P is a water soluble polymer having functional groups compatible with forming covalent bonds with the ligand or a spacer; a is 0 or 1; and c and d are integers of at least 1.

10. The composition of claim 9 wherein P is a polyalkylene oxide.

11. The composition of claim 10 wherein said polyalkylene oxide is a member selected from the group consisting of alpha-substituted polyalkylene oxide derivatives, polyethylene glycol homopolymers and derivatives thereof, polypropylene glycol homopolymers and derivatives thereof, alkyl-capped polyethylene oxides, bis-polyethylene oxides, copolymers of poly(alkylene oxides), branched polyethylene glycols, star polyethylene glycols, and block copolymers of poly(alkylene oxides) or activated derivatives thereof.

12. The composition of claim 10 wherein said polyalkylene oxide has a molecular weight of about 200 to about 50,000.

13. The composition of claim 10 wherein said polyalkylene oxide has a molecular weight of about 2,000 to about 20,000.

14. The composition of claim 10 wherein said polyalkylene oxide has a molecular weight of about 20,000.

15. The composition of claim 10 wherein said polyalkylene oxide is an activated polyethylene glycol.

16. The composition of claim 15 wherein said activated polyethylene glycol is a branched polyethylene glycol.

17. The composition of claim 10 wherein said polyalkylene oxide is a polyethylene oxide.

18. The composition of claim 1 wherein said IL-2-receptor binding peptide is SEQ ID NO:46.

19. The composition of claim 3 wherein said chemical agent is a label.

20. The composition of claim 19 wherein said label is selected from the group consisting of fluorescent labels, radioactive labels, and magnetic labels.

21. The composition of claim 1 wherein said chemical agent is a drug.

22. The composition of claim 9 wherein said spacer comprises a peptide.

23. The composition of claim 22 wherein said peptide is enzyme-cleavable.

24. The composition of claim 22 wherein said peptide comprises Gly-Phe-Leu-Gly (SEQ ID NO:21).

25. The composition of claim 1, wherein the polymer comprises a polyalkylene oxide.

26. The composition of claim 25, wherein the polyalkylene oxide is a polyethylene oxide.

27. The composition of claim 25, wherein the polyalkylene oxide is selected from the group consisting of alpha-substituted polyalkylene oxide derivatives, polyethylene glycol homopolymers and derivatives thereof, polypropylene glycol homopolymers and derivatives thereof, alkyl-capped polyethylene oxides, bis-polyethylene oxides, copolymers of poly(alkylene oxides), branched polyethylene glycols, star polyethylene glycols, and block copolymers of poly(alkylene oxides) or activated derivatives thereof.

* * * * *

```
                          SEQUENCE LISTING

<160> NUMBER OF SEQ ID NOS: 47

<210> SEQ ID NO: 1
<211> LENGTH: 6
<212> TYPE: PRT
<213> ORGANISM: Homo sapiens

<400> SEQUENCE: 1

Leu Glu His Leu Leu Leu
1               5

<210> SEQ ID NO: 2
<211> LENGTH: 6
<212> TYPE: PRT
<213> ORGANISM: Artificial Sequence
<220> FEATURE:
<223> OTHER INFORMATION: Found in HTLV-III, this sequence exhibits
      similarity to a sequence found in human IL-2.

<400> SEQUENCE: 2

Leu Glu Arg Ile Leu Leu
1               5

<210> SEQ ID NO: 3
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 3

Leu Glu Arg Leu Leu Leu
1               5

<210> SEQ ID NO: 4
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 4

Leu Asp Leu Leu Phe Trp
1               5

<210> SEQ ID NO: 5
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 5

Leu Asp Leu Leu Phe Leu
1               5
```

```
<210> SEQ ID NO: 6
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 6

Leu Asp Ile Leu Phe Leu
 1               5

<210> SEQ ID NO: 7
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 7

Leu Gln His Leu Phe Leu
 1               5

<210> SEQ ID NO: 8
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 8

Leu Glu His Ile Leu Leu
 1               5

<210> SEQ ID NO: 9
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 9

Leu Gln His Ile Leu Leu
 1               5

<210> SEQ ID NO: 10
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 10

Leu Asp His Ile Phe Leu
 1               5

<210> SEQ ID NO: 11
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.
```

```
<400> SEQUENCE: 11

Leu Asn His Ile Phe Leu
 1               5

<210> SEQ ID NO: 12
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 12

Gln His Leu Phe Leu Gly
 1               5

<210> SEQ ID NO: 13
<211> LENGTH: 8
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 13

Gly Leu Gln His Leu Phe Leu Gly
 1               5

<210> SEQ ID NO: 14
<211> LENGTH: 11
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 14

Gly Leu Glu Arg Ile Leu Leu Gly Phe Leu Gly
 1               5                  10

<210> SEQ ID NO: 15
<211> LENGTH: 11
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 15

Gly Leu Glu His Ile Leu Leu Gly Phe Leu Gly
 1               5                  10

<210> SEQ ID NO: 16
<211> LENGTH: 11
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 16

Gly Leu Gln His Ile Leu Leu Gly Phe Leu Gly
 1               5                  10

<210> SEQ ID NO: 17
<211> LENGTH: 11
```

```
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 17

Gly Leu Asp His Ile Phe Leu Gly Phe Leu Gly
1               5                   10

<210> SEQ ID NO: 18
<211> LENGTH: 11
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 18

Gly Leu Asn His Ile Phe Leu Gly Phe Leu Gly
1               5                   10

<210> SEQ ID NO: 19
<211> LENGTH: 12
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 19

Thr Gly Leu Gln His Ile Leu Leu Gly Phe Leu Gly
1               5                   10

<210> SEQ ID NO: 20
<211> LENGTH: 11
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 20

Ser Leu Gln His Ile Leu Leu Gly Phe Leu Gly
1               5                   10

<210> SEQ ID NO: 21
<211> LENGTH: 4
<212> TYPE: PRT
<213> ORGANISM: Artificial Sequence
<220> FEATURE:
<223> OTHER INFORMATION: biodegradable spacer sequence

<400> SEQUENCE: 21

Gly Phe Leu Gly
1

<210> SEQ ID NO: 22
<211> LENGTH: 12
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 22

Thr Gly Leu Asn Arg Ile Leu Leu Gly Phe Leu

<210> SEQ ID NO: 23
<211> LENGTH: 12
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 23

Thr Gly Leu Asn Arg Leu Leu Leu Gly Phe Leu Gly
 1               5                  10

<210> SEQ ID NO: 24
<211> LENGTH: 8
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 24

Thr Gly Leu Asp Arg Ile Leu Leu
 1               5

<210> SEQ ID NO: 25
<211> LENGTH: 8
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 25

Thr Gly Leu Asp Arg Leu Leu Leu
 1               5

<210> SEQ ID NO: 26
<211> LENGTH: 8
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 26

Thr Gly Leu Asn Arg Leu Leu Leu
 1               5

<210> SEQ ID NO: 27
<211> LENGTH: 8
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 27

Thr Gly Leu Asn Arg Ile Leu Leu
 1               5

<210> SEQ ID NO: 28
<211> LENGTH: 9
<212> TYPE: PRT
<213> ORGANISM: Artificial Sequence
<220> FEATURE:
<223> OTHER INFORMATION: Exhibits sequence similarity to a portion of
      human IL-2.

```
<400> SEQUENCE: 28

Thr Gly Leu Asp Arg Ile Phe Leu Gly
 1               5

<210> SEQ ID NO: 29
<211> LENGTH: 9
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 29

Thr Gly Leu Asp Arg Leu Phe Leu Gly
 1               5

<210> SEQ ID NO: 30
<211> LENGTH: 9
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 30

Thr Gly Leu Asn Arg Ile Phe Leu Gly
 1               5

<210> SEQ ID NO: 31
<211> LENGTH: 9
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 31

Thr Gly Leu Asn Arg Leu Phe Leu Gly
 1               5

<210> SEQ ID NO: 32
<211> LENGTH: 7
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 32

Gly Leu Asn Arg Ile Leu Leu
 1               5

<210> SEQ ID NO: 33
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 33

Leu Asp Arg Ile Leu Leu
 1               5

<210> SEQ ID NO: 34
<211> LENGTH: 7
```

```
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 34

Gly Leu Asp Arg Leu Leu Leu
 1               5

<210> SEQ ID NO: 35
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 35

Leu Asp Arg Leu Leu Leu
 1               5

<210> SEQ ID NO: 36
<211> LENGTH: 7
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 36

Gly Leu Asn Arg Leu Leu Leu
 1               5

<210> SEQ ID NO: 37
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 37

Leu Asn Arg Leu Leu Leu
 1               5

<210> SEQ ID NO: 38
<211> LENGTH: 7
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 38

Gly Leu Asn Arg Ile Leu Leu
 1               5

<210> SEQ ID NO: 39
<211> LENGTH: 6
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 39

Leu Asn Arg Ile Leu Leu
```

```
1               5

<210> SEQ ID NO: 40
<211> LENGTH: 8
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 40

Gly Leu Asp Arg Ile Phe Leu Gly
1               5

<210> SEQ ID NO: 41
<211> LENGTH: 7
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 41

Leu Asp Arg Ile Phe Leu Gly
1               5

<210> SEQ ID NO: 42
<211> LENGTH: 8
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 42

Gly Leu Asp Arg Leu Phe Leu Gly
1               5

<210> SEQ ID NO: 43
<211> LENGTH: 7
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 43

Leu Asp Arg Leu Phe Leu Gly
1               5

<210> SEQ ID NO: 44
<211> LENGTH: 8
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 44

Gly Leu Asn Arg Ile Phe Leu Gly
1               5

<210> SEQ ID NO: 45
<211> LENGTH: 7
<212> TYPE: PRT
<213> ORGANISM: Artificial Sequence
<220> FEATURE:
<223> OTHER INFORMATION: Exhibits sequence similarity to a portion of
```

-continued

```
       human IL-2.

<400> SEQUENCE: 45

Leu Asn Arg Ile Phe Leu Gly
 1               5

<210> SEQ ID NO: 46
<211> LENGTH: 8
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 46

Gly Leu Asn Arg Leu Phe Leu Gly
 1               5

<210> SEQ ID NO: 47
<211> LENGTH: 7
<212> TYPE: PRT
<213> ORGANISM: Artificial Sequence
<220> FEATURE:
<223> OTHER INFORMATION: Exhibits sequence similarity to a portion of
      human IL-2.

<400> SEQUENCE: 47

Leu Asn Arg Leu Phe Leu Gly
 1               5
```